US005627214A

United States Patent [19]
Schäfer et al.

[11] Patent Number: 5,627,214
[45] Date of Patent: May 6, 1997

[54] USE OF DIAMINES IN OPHTHALMIC COMPOSITIONS

[75] Inventors: Rolf Schäfer, Bubendorf, Switzerland; Ronald L. Schlitzer, Fort Worth; Nissanke L. Dassanayake, Arlington, both of Tex.

[73] Assignee: Alcon Laboratories, Inc., Fort Worth, Tex.

[21] Appl. No.: 389,669

[22] Filed: Feb. 16, 1995

Related U.S. Application Data

[62] Division of Ser. No. 142,624, Oct. 25, 1993, Pat. No. 5,415,837.

[51] Int. Cl.$^6$ .................................................. A61K 31/14
[52] U.S. Cl. .................................... 514/642; 514/912
[58] Field of Search ................................. 514/642, 912

[56] References Cited

U.S. PATENT DOCUMENTS

| | | | |
|---|---|---|---|
| 3,206,462 | 9/1965 | McCarty | 260/256.4 |
| 3,943,255 | 3/1976 | Newkirk | 424/329 |
| 4,407,791 | 10/1983 | Stark | 424/80 |
| 5,171,526 | 12/1992 | Wong et al. | 422/28 |

*Primary Examiner*—Zohreh Fay
*Attorney, Agent, or Firm*—James A. Arno; Gregg C. Brown

[57] ABSTRACT

Certain alkenyl diamines, the use of same for disinfecting and cleaning contact lenses and preserving ophthalmic products, and associated ophthalmic compositions are described.

4 Claims, No Drawings

USE OF DIAMINES IN OPHTHALMIC COMPOSITIONS

This is a Division, of application Ser. No. 08/142,624, filed Oct. 25, 1993 now U.S. Pat. No. 5,415,837.

BACKGROUND OF THE INVENTION

The present invention relates to the field of ophthalmology. More particularly, the invention is directed to compositions and methods for disinfecting and cleaning contact lenses, and to the chemical preservation of various types of ophthalmic products.

Contact lenses are exposed to a broad spectrum of microbes during normal wear and become soiled relatively quickly. Routine cleaning and disinfecting of the lenses are therefore required. Although the frequency of cleaning and disinfecting may vary somewhat among different types of lenses and lens care regimens, daily cleaning and disinfecting is normally required. Failure to clean and disinfect the lens properly can lead to a multitude of problems ranging from mere discomfort when the lenses are being worn to serious ocular infections. Ocular infections caused by particularly virulent microbes, such as *Pseudomonas aeruginosa*, can lead to loss of the infected eye(s) if left untreated or if allowed to reach an advanced stage before treatment is initiated. It is therefore extremely important that patients disinfect their contact lenses in accordance with the regimen prescribed by their optometrist or ophthalmologist.

Unfortunately, patients frequently fail to follow the prescribed regimens. Many patents find regimens to be difficult to understand and/or complicated, and as a result do not comply with one or more aspects of the regimen. Other patients may have a negative experience with the regimen, such as ocular discomfort attributable to the disinfecting agent, and as a result do not routinely disinfect their lenses or otherwise stray from the prescribed regimen. In either case, the risk of ocular infections is exacerbated.

Despite the availability of various types of contact lens disinfecting systems, such as heat, hydrogen peroxide, and other chemical agents, there continues to be a need for improved systems which: 1) are simple to use, 2) have potent antimicrobial activity, and 3) are nontoxic (i.e., do not cause ocular irritation as the result of binding to the lens material). Moreover, the chemical agents utilized in the currently marketed contact lens disinfection systems generally have limited antifungal activity. Also, many of the chemical agents currently utilized may interact with contact lens materials and/or cause irritation in some individuals. There is, therefore, a particular need in the fields of contact lens disinfection and ophthalmic composition preservation for safe and effective chemical agents having better antifungal activity. The present invention is directed to satisfaction of the above-cited needs.

SUMMARY OF THE INVENTION

The present invention is directed to methods of using certain diamines to disinfect contact lenses and to preserve ophthalmic compositions. The invention is also directed to contact lens disinfecting compositions which contain one or more of the subject compounds, and to various types of ophthalmic compositions (e.g., pharmaceuticals, artificial tears and comfort drops) which contain the compounds for purposes of preserving the compositions against microbial contamination.

In addition to having antimicrobial activity, including both antibacterial and antifungal activity, the compounds of the present invention are also surface active. As a result, the compounds also help to clean contact lenses by facilitating the removal of deposits from the lenses.

The diamines of the present invention retain their antimicrobial activity in the presence of $Na^+$, $Ca^{++}$, $Cl^-$ and other inorganic ions produced by the dissociation of alkaline and alkaline earth metal salts (e.g., sodium chloride and calcium chloride), and are compatible with polymers and surfactants frequently used in ophthalmic products, such as polyvinylpyrrolidone, and polyoxyethylene/polyoxypropylene copolymers of ethylene diamines.

DESCRIPTION OF PREFERRED EMBODIMENTS

The compounds used in the present invention comprise one or more compounds of the following formula, or pharmaceutically acceptable salts thereof (e.g., hydrohalide salts):

$$R\text{—NH—}(CH_2)_n\text{—}NH_2 \quad \quad (I)$$

wherein: R is $C_6$ to $C_{18}$ saturated or unsaturated alkyl, alkylaryl or alkoxyaryl; and n is 2 to 16, preferably 2 to 4. When R is alkenyl, the compounds of formula (I) above may be in either the cis or trans configuration.

The following compounds of formula (I) are particularly preferred:

| Compound No. | R | n |
|---|---|---|
| 1 | oleyl | 3 |
| 2 | stearyl | 3 |
| 3 | cetyl | 3 |
| 4 | myristyl | 3 |
| 5 | lauryl | 3 |

The most preferred compound of formula (I) is:

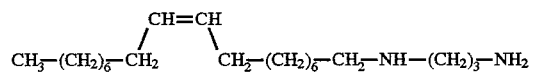

This compound is known as N-oleyl-1,3-diaminopropane.

The compounds of formula (I) are known. Such compounds are described in U.S. Pat. Nos. 3,206,462 and 3,943,255. The entire contents of both of the above-cited patents are hereby incorporated in the present specification by reference. The above-cited patents do not describe the use of compounds of formula (I) as disinfectants or preservatives in ophthalmic products, particularly products used in the care of contact lenses.

The compounds of formula (I) may be prepared by means of known methods. The preferred method of synthesis for preparing N-oleyl-1,3-diaminopropane is outlined below; analogous methods may be utilized to prepare the other compounds of formula (I):

Synthesis

Step 1:

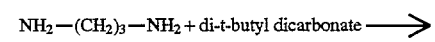

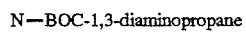

N—BOC-1,3-diaminopropane

-continued
Synthesis

Step 2:

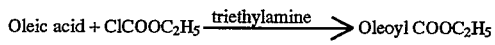

Step 3:

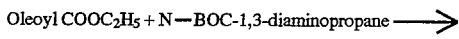

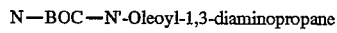

Step 4:

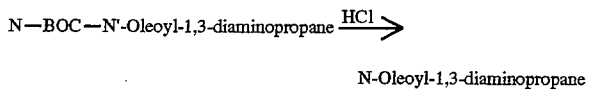

Step 5:

The compounds of formula (I) can be used individually, in combination with one or more other compounds of formula (I), or in combination with other disinfectants or preservatives. The compounds may, for example, be used in combination with the polymeric quaternary ammonium compounds described in U.S. Pat. No. 4,407,791; the entire contents of that patent are hereby incorporated in the present specification by reference. As described in the '791 patent, those polymeric quaternary ammonium compounds are useful in disinfecting contact lenses and preserving ophthalmic compositions.

The amount of each compound used will depend on the purpose of the use, e.g., disinfection of contact lenses or preservation of ophthalmic products, and the absence or inclusion of other antimicrobial agents. The concentrations determined to be necessary for the above-stated purposes can be functionally described as "an amount effective to disinfect" and "an amount effective to preserve" or variations thereof. The concentrations used for disinfection will generally be in the range of from about 0.0001 to about 0.1 percent by weight based on the total weight of the composition ("wt. %"). The concentrations used for preservation will generally be in the range of from about 0.00001 to about 0.01 wt. %.

The compounds of formula (I) may be included in various types of ophthalmic compositions as preservatives, so as to prevent microbial contamination of the compositions. The types of compositions which may be preserved by the compounds of formula (I) include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of compositions, such as ocular lubricating products, artificial tears, astringents, and so on. The compositions may be aqueous or nonaqueous, but will generally be aqueous. As will be appreciated by those skilled in the art, the compositions may contain a wide variety of ingredients, such as tonicity agents (e.g., sodium chloride or mannitol), surfactants (e.g., polyvinyl pyrrolidone and polyoxyethylene/polyoxypropylene copolymers), viscosity adjusting agents (e.g., hydroxypropyl methyl cellulose and other cellulose derivatives) and buffering agents (e.g., borates, citrates, phosphates and carbonates). The present invention is not limited with respect to the types of ophthalmic compositions in which the compounds of formula (I) may be contained as preservatives. In fact, as already noted above, the compatibility of the compounds of formula (I) with other ingredients of ophthalmic compositions, such as inorganic ions, polymers and surfactants, is a distinct advantage of the present invention, relative to antimicrobial agents previously utilized in the ophthalmic field.

As with the ophthalmic compositions of the present invention which contain one or more compounds of formula (I) as preservatives, the form of the compositions of the present invention containing one or more of the compounds for purposes of disinfecting contact lenses is not limited. The contact lens disinfecting compositions of the present invention will preferably be formulated as aqueous solutions, but may also be formulated as nonaqueous solutions, as well as suspensions, gels, and so on. The compositions may contain a variety of tonicity agents, surfactants, viscosity adjusting agents and buffering agents, as described above. The chemical compatibility of the compounds of formula (I) is also a significant advantage with respect to the use of these compounds in the contact lens disinfecting compositions of the present invention.

The above-described compositions may be used to disinfect contact lenses in accordance with processes known to those skilled in the art. More specifically, the lenses will first be removed from the eyes of the patients, and then will be immersed in the compositions for a time sufficient to disinfect the lenses. This immersion will typically be accomplished by means of soaking the lenses in a solution overnight (i.e., approximately six to eight hours). The lenses will then be rinsed and placed in the eye. Prior to immersion in the disinfecting compositions, the lenses will preferably also be cleaned and rinsed.

The compounds of formula (I) also have surface active properties. As a result of these properties, the compounds are also useful in cleaning contact lenses. More specifically, the surfactant properties of the compounds facilitate the removal of deposits typically accumulated on contact lenses when worn by human patients. These deposits vary from patient to patient, but will typically include proteins, lipids, polysaccharides and mixtures thereof, as well as various other soils which may accumulate on the lenses during normal wear and handling. The compounds will exhibit some cleaning effect even at the relatively low concentrations required for purposes of preserving ophthalmic compositions or disinfecting contact lenses. This cleaning effect is therefore useful as a supplement to the effect of other cleaning agents which may be contained in the compositions, such as anionic or nonionic surfactants. Moreover, when used at a concentration of 0.01 wt.% or higher, the compounds exhibit a more pronounced cleaning effect. The manner in which the cleaning effect of the compounds of formula (I) is utilized will depend on the type of contact lens being treated, the severity and type of the deposits on the lenses, and the overall treatment regimen used by the patient. The selection of other components for inclusion in the contact lens cleaning compositions of the present invention will also depend on these factors. The cleaning compositions will generally contain one or more of the compounds of formula (I) in an amount of at least 0.01 wt. %, and preferably from about 0.01 to 1.0 wt. %.

The above-described compositions may be used to clean contact lenses in accordance with known processes. For example, the lenses, after first being removed from the eye and preferably also rinsed, may be lightly rubbed with a small amount of the compositions between the fingers, or may be immersed in a somewhat larger volume of the compositions and then allowed to soak. The lenses are then rinsed and disinfected before being replaced in the eyes of the patients.

All of the above-described compositions will be formulated so as to be compatible with the eye and/or contact lenses to be treated with the compositions. As will be appreciated by those skilled in the art, the ophthalmic compositions; intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition to a level at or near 300–320 milliosmoles. The formulation of compositions for disinfecting and/or cleaning contact lenses will involve similar considerations, as well as considerations relating to the physical effect of the compositions on contact lens materials and the potential for binding or absorption of the components of the composition by the lens.

The compositions and methods of the present invention may be used in conjunction with various types of contact lenses, including both lenses generally classified as "hard" and lenses generally classified as "soft".

The following examples are presented to further illustrate ophthalmic compositions which may contain one or more of the compounds of formula (I):

EXAMPLE 1

The following formulation might serve as a vehicle for an ophthalmic drag. The formulation would contain one or more compounds of formula (I) as a preservative.

| Ingredient | Amount (wt. %) |
|---|---|
| Sodium Chloride | 0.5% |
| Mannitol | 2.5% |
| HEPES | 0.119% |
| NaOH/HCl | pH 7.0 |
| Purified water | QS 100 |

EXAMPLE 2

The following formulation may be utilized as a contact lens disinfecting solution. The formulation would contain one or more compounds of formula (I) as a disinfectant.

| Ingredient | Amount (wt. %) |
|---|---|
| Mannitol | 0.64% (w/v) |
| Boric Acid | 0.225% |
| Sodium Borate | 0.08% |
| Sodium Citrate | 0.46% |
| Citric Acid | 0.016% |
| Sodium Chloride | 0.48% |
| Disodium Edetate | 0.05% |
| NaOH/HCl | pH 7.0 |
| Purified Water | QS 100 |

EXAMPLE 3

The following formulation may be utilized as a contact lens disinfecting solution, and would also aid in the cleaning of the lens.

| Ingredient | Amount (wt. %) |
|---|---|
| Compound No. 4 | 0.01% |
| Boric Acid | 0.58% |
| Sodium Borate | 0.18% |
| Sodium Chloride | 0.49% |
| Disodium Edetate | 0.05% |
| Poloxamine | 0.1% |

-continued

| Ingredient | Amount (wt. %) |
|---|---|
| NaOH/HCl | pH 7.0 |
| Purified Water | QS 100% |

The following example is presented to further illustrate the preferred method of synthesizing the compounds of formula (I), and in particular Compound No. 1:

EXAMPLE 4

Synthesis of N-Oleyl-1,3-Diaminopropane Dihydrochloride 1,3-Diaminopropane (379 ml) was dissolved in methanol and treated with di-t-butyl dicarbonate (95 g.) to provide N-BOC-1,3-diaminopropane. Distillation yielded 60 g. of clear oil. GC analysis showed 93% purity; however, no 1,3-diaminopropane was present.

In tetrahydrofuran, oleic acid was first treated with triethylamine (108 ml) and ethyl chloroformate (41 ml), and then with N-BOC-1,3-diaminopropane (60 g.). The yield of N-BOC-N'-oleoyl-1,3-diaminopropane was 1.55 g. as crude product.

Deprotection of crude N-BOC-N'-oleoyl-1,3-diaminopropane (155 g.) with aqueous hydrochloric acid in tetrahydrofuran yielded 125 g. of N-oleoyl-1,3-diaminopropane.

Lithium aluminum hydride reduction of a tetrahydrofuran solution of N-oleoyl-1,3-diaminopropane furnished N-oleyl-1,3-diaminopropane. Purification was performed by acidifying an ether solution with a tetrahydrofuran solution of hydrogen chloride and filtering the precipitated product. The free amine was regenerated by treatment with aqueous sodium hydroxide and again treated with hydrogen chloride in tetrahydrofuran to precipitate the product as the dihydrochloride salt. Final purification was performed by dissolving the hydrochloride salt in boiling isopropanol, filtration, partial concentration of the filtrate, and chilling to effect precipitation. The precipitate product was filtered, rinsed with ether, and dried under vacuum to yield 34 g. (25% from oleic acid). Analysis: Calculated for $C_{21}H_{46}N_2Cl_2$: C, 63.45; H, 11.66; N, 7.05; Cl, 17.84. Found: C, 63.56; H, 11.76; N, 7.03; Cl, 18.04. Assay by titration 97.5; Assay by G.C. 92.7%.

What is claimed is:

1. A method of preserving an ophthalmic composition which comprises including in the composition an amount of a compound of the following formula effective to preserve the composition from microbial contamination:

$$R-NH-(CH_2)_n-NH_2 \qquad (I)$$

wherein: R is $C_6$ to $C_{18}$ saturated or unsaturated alkyl, alkylaryl or alkoxyaryl, and n is 2 to 16, or a pharmaceutically acceptable salt thereof; and a pharmaceutically acceptable vehicle therefor.

2. A method according to claim 1, wherein n is 2 to 4.

3. A method according to claim 2, wherein R is selected from the group consisting of oleyl, stearyl, cetyl, myristyl and lauryl.

4. A method according to claim 1, wherein the compound comprises N-oleyl-1,3-diaminopropane.

* * * * *